United States Patent
Greneker III et al.

(10) Patent No.: US 6,909,397 B1
(45) Date of Patent: Jun. 21, 2005

(54) STABILIZING MOTION IN A RADAR DETECTION SYSTEM USING ULTRASONIC RADAR RANGE INFORMATION

(75) Inventors: Eugene Ferguson Greneker III, Marietta, GA (US); Daren Joseph Zywicki, Smyrna, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 6 days.

(21) Appl. No.: 10/732,126

(22) Filed: Dec. 10, 2003

(51) Int. Cl.[7] ................. G01S 13/88; G01S 13/86; G01S 7/40
(52) U.S. Cl. ............. 342/173; 342/22; 342/27; 342/28; 342/52; 342/53; 342/54; 342/59; 342/159; 342/165; 342/175; 342/195; 356/4.01; 356/72; 367/87; 367/93; 367/94; 367/95; 367/97
(58) Field of Search ............. 367/87–116, 900, 367/901, 903, 904, 910, 911; 342/22, 25 R–25 F, 27, 28, 52–55, 59, 70–72, 82–103, 118, 127, 128, 131, 132, 134, 135, 159, 165–175, 189–197; 128/204.21, 204.22, 204.23; 356/4.01–5.15, 72; 340/521, 551–557, 435; 600/407, 430, 529, 534, 535, 536

(56) References Cited

U.S. PATENT DOCUMENTS

| | | | | |
|---|---|---|---|---|
| 3,796,208 A | * | 3/1974 | Bloice | 600/534 |
| 3,864,660 A | * | 2/1975 | Ranalli et al. | 367/113 |
| 3,993,995 A | * | 11/1976 | Kaplan et al. | 342/194 |
| 4,031,743 A | * | 6/1977 | Kossoff et al. | 367/900 |
| 4,164,740 A | * | 8/1979 | Constant | 342/25 R |
| 4,625,199 A | * | 11/1986 | Pantus | 340/521 |
| 4,958,638 A | | 9/1990 | Sharpe et al. | 128/653 R |
| 4,967,751 A | * | 11/1990 | Sterzer | 600/407 |
| 5,030,956 A | * | 7/1991 | Murphy | 342/22 |
| 5,206,652 A | * | 4/1993 | Hoyt et al. | 342/52 |
| 5,573,012 A | * | 11/1996 | McEwan | 600/534 |
| 5,754,123 A | * | 5/1998 | Nashif et al. | 340/435 |
| 6,062,216 A | * | 5/2000 | Corn | 128/204.23 |
| 6,122,537 A | | 9/2000 | Schmidt | 600/407 |
| 6,208,286 B1 | | 3/2001 | Rostislavovich et al. | 342/135 |
| 6,492,933 B1 | * | 12/2002 | McEwan | 342/28 |
| 6,736,231 B2 | * | 5/2004 | Breed et al. | 342/72 |

OTHER PUBLICATIONS

U.S. Appl. No. 10/735,478, filed Dec. 12 2003, entitled, "Radar Detection Device Employing a Scanning Antenna System."

* cited by examiner

*Primary Examiner*—Bernarr E. Gregory
(74) *Attorney, Agent, or Firm*—Thomas, Kayden, Horstemeyer & Risley

(57) ABSTRACT

One preferred embodiment of the present invention provides a system and method for suppressing motion artifacts introduced by movement of a radar detection system. Briefly described, in architecture, one embodiment of the system, among others, can be implemented as follows. The system includes a Doppler radar module configured to transmit a microwave signal directed towards an object and receive the reflected microwave signals from the object and a living subject positioned behind the object. Also, the system includes a reference module configured to transmit a reference signal towards the object and receive the reflected reference signal from the object. By comparing the two reflected signals from the Doppler radar module and the reference device, a signal processor suppresses motion artifacts generated by movement of the Doppler radar module to identify the presence of the living subject behind the object. Other systems and methods are also provided.

39 Claims, 7 Drawing Sheets

“STABILIZING MOTION IN A RADAR DETECTION SYSTEM USING ULTRASONIC RADAR RANGE INFORMATION”

TECHNICAL FIELD

The present invention is generally related to microwave radar systems and, more particularly, is related to systems and methods for detecting vital signs, through a non-conducting intervening wall with a microwave radar system.

BACKGROUND OF THE INVENTION

One recent use of homodyne radar system involves the detection of minute body movements which are associated with human respiratory activity. This approach is based on the principle that breathing produces measurable phase changes in electromagnetic waves as they reflect off of the skin surface of the moving thorax of a living person. When the skin surface is moving, as does the surface of the chest in conjunction with respiratory and cardiac activities, corresponding variations will be observed in the difference of the phase between the received and transmitted signal. The observed variations can be used to determine motion-related target parameters such as displacement and velocity.

Given the extreme sensitivity to slight motion that can be sensed with homodyne radar, a device has been developed and designed called a "Radar Flashlight." The Radar Flashlight is designed to allow police or the military to detect the respiration signature of a non-cooperative human subject behind a wall, door or an enclosed space with non-conductive walls. The device also has application to the location of conscious or unconscious persons in a smoke filled or chemical contaminated office building.

Currently, in operation, the Radar Flashlight is placed against the intervening wall or on a tripod and the homodyne radar system is activated by the operator. When the Radar Flashlight is not stabilized by the user pressing it against the wall or by placing it on a stabilizing tripod, the user's slight hand motion is detected by the Radar Flashlight as movement. Thus, when hand motion is present, the homodyne radar cannot effectively determine if the detected movement signature is from the subject or from the stationary wall.

Thus, a heretofore unaddressed need exists in the industry to address the aforementioned deficiencies and inadequacies.

SUMMARY OF THE INVENTION

The present invention provides systems and methods for detecting a respiration signal in a target area while rejecting hand motion clutter. One such system among, others, is briefly described in architecture as follows. The system includes a Doppler radar module configured to transmit a microwave signal directed towards an object, such as a wall or other non-conducting object, while simultaneously receiving the reflected microwave signal from the object and a living subject positioned behind the obstructing wall or other non-conducting object. Also, the system includes a reference module attached to the radar detection device and configured to transmit a reference signal towards the wall or other non-conducting object obscuring the living subject and receive the reflected reference signal from the wall or other non-conducting object obscuring the living subject. By comparing information obtained from the received reflected signals from the Doppler radar module and the reference module, the presence of the living subject behind the wall may be positively determined.

Briefly described, one embodiment of a method, among others, for suppressing motion artifacts introduced by movement of a radar detection device comprises the steps of: transmitting a first beam of microwave energy towards an object; receiving reflected energy from the first beam of microwave energy, the reflected microwave energy from the first beam comprising a reflected microwave signal from the object; transmitting a reference beam of energy towards the object; and receiving reflected reference energy from the reference beam of energy, the reflected reference energy from the reference beam comprising a reflected reference signal from the object.

Other features and advantages of the present invention will be or become apparent to one with skill in the art upon examination of the following drawings and detailed description. It is intended that all such additional systems, methods, features, and advantages be included within this description, be within the scope of the present invention.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

DETAILED DESCRIPTION

Figure 1:
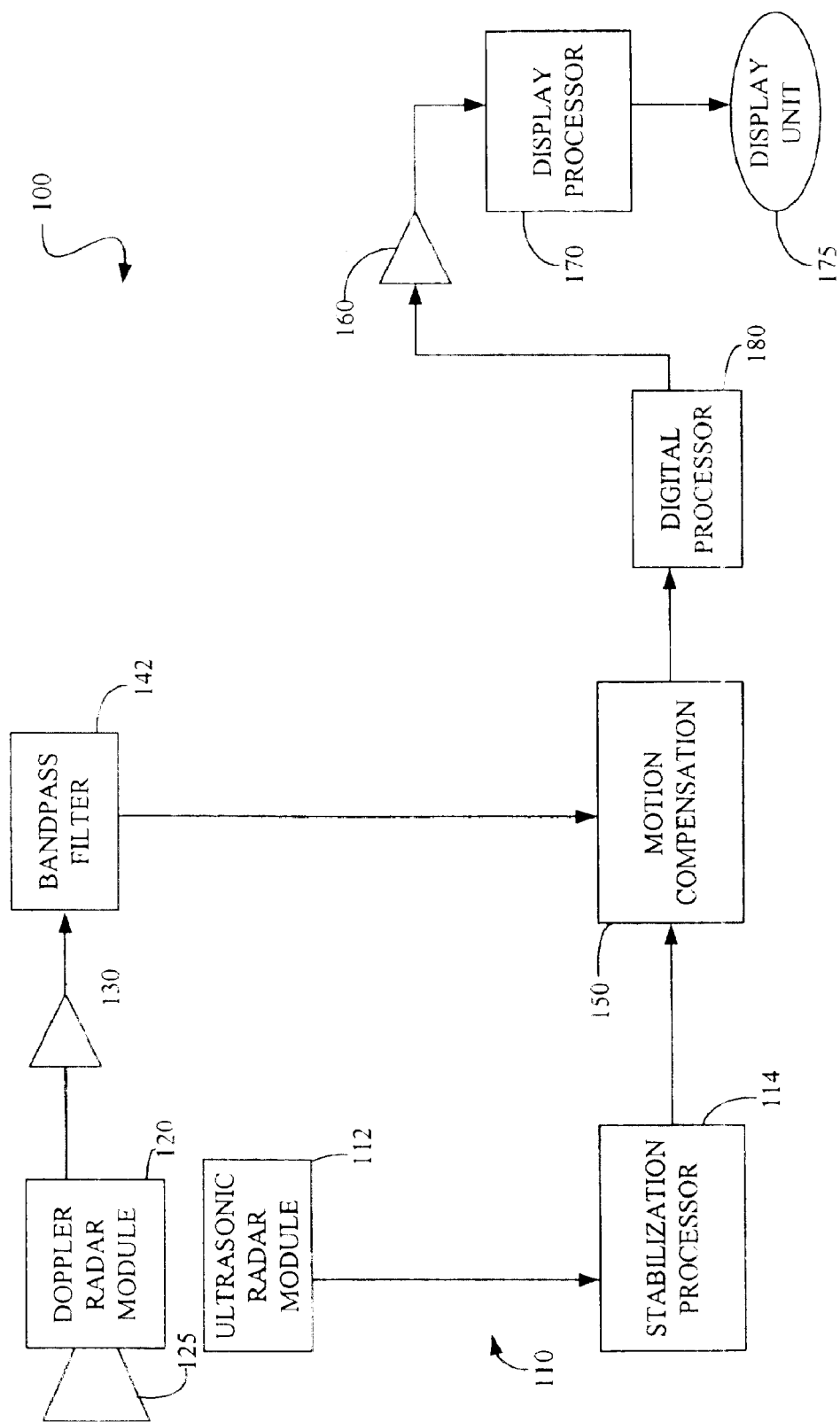
FIG. 1 is a block diagram of an embodiment of a radar detection system employing an embodiment of a stabilization system of the present invention.

FIG. 1 shows a diagram of one embodiment of a radar detection device (100) employing one embodiment of the stabilization system (110) of the present invention. In this example, the radar detection device (100) comprises a Doppler radar module (120) that generates a microwave continuous wave (CW) signal at 10.525 GHz. However, other microwave frequencies may also be used.

The CW signal is generated using a solid state Gunn device transmitter (not shown). The resulting CW signal is transmitted through an antenna (125). When a person, for example, is located in front of the antenna (125), the transmitted signal is reflected off the body of the target individual. Thus, any motion of the person's body causes a phase shift in the reflected signal proportional to the amount of motion in the radial direction to the Doppler radar module (120). At a frequency of 10.525 GHz, for example, the typical phase shift is 360 degrees for every 1.75 centimeters of radial motion toward or way from the Doppler radar module (120) and antenna (125).

The Doppler radar module (120) of the radar detection device (100) transmits microwave energy in a 16-degree beam toward its target. If the target is a subject positioned behind a wall, a high percentage of the transmitted power incident on the wall is reflected back to the Doppler radar module (120) of the radar detection device (100). In addition, a low percentage of the transmitted power actually penetrates the wall to "illuminate" the subject of interest.

Accordingly, a small amount of the incident illuminating energy is reflected off of the subject's thorax, back through the wall, and to the radar detection device's antenna (125). The signal reflected from the subject is received by the antenna (125) and sent to the Doppler radar module (120), where a reference signal from the CW transmitter is mixed with the received signal. A sum and difference signal is generated during the mixing process in typical homodyne fashion. The sum signal is filtered and eliminated while the difference signal is sent to preamplifier (130). The gain of pre-amplifier (130) is set so that it does not saturate on the maximum expected signal. The output of pre-amplifier (130) is fed to bandpass filter (142). The input to bandpass filter (142) contains the respiration signal and inteference. Accordingly bandpass filter (142) removes the radar clutter signals caused by fluorescent light plasma modulation. The bandpass filter (142) also passes any signal caused by radar detection device motion that falls within the bandpass of the filter (142). The filtered signal is passed to the motion compensation module (150), where the very large radar clutter contribution caused by the radar detection device's motion is removed in a manner to be described below.

There are two primary types of motion to be eliminated with respect to the radar detection device (100): (1) the velocity of the moving arm of the user and (2) the body motion of the user. When the radar detection device (100) is hand-held and the user is moving, there is motion from both the user's body and arm. Therefore, all fixed objects illuminated by the antenna beam reflect some energy that appears to have motion due to the hand and arm motion of the operator.

While the fixed objects in the antenna beam do not move and would normally not cause a phase shift, the signal from the fixed objects is phase shifted because the radar detection device (100) is moving with the body of the user. Note, the Doppler shifted backscatter from fixed objects tend to be a very large amplitude signal compared to the low amplitude signal generated by the small amount of chest cavity motion of a targeted subject during respiration. Therefore, the motion that should be cancelled is the motion of the operator holding the radar detection device (100) in his or her hand. This task is performed by the stabilization system (110).

The stabilization system (110) includes a reference module (112) that is linked to the radar detection device assembly. In this particular embodiment, the reference module is an ultrasonic radar module (112) that transmits and receives an ultrasonic signal that is used as a source of reference or baseline information in analyzing the signal received by the Doppler radar module (120). Note, in some embodiments, reference or baseline data may be determined from the signals received by the reference module using other types of signals. For example, laser technology, among others, may be used in lieu of ultrasonic technology.

Accordingly, in some embodiments, the ultrasonic radar module (112) transmits a continuous signal at a sonic frequency and detects the difference between the phase of the transmitted signal and received signal. The frequency of the ultrasonic radar's continuous wave transmission is selected so that the phase shift caused by an operator's hand motion produces the same phase shift at the ultrasonic frequency of operation as the microwave radar signal reflecting from the wall target at microwave frequencies. The phase shift from the homodyne ultrasonic radar is mathematically manipulated to align it to the starting phase and magnitude as the motion induced phase shift detected by the Doppler radar module (120). Because the motion signal produced by movement of the radar detection device is identical from both the ultrasonic radar (112) and microwave radar (120) modules, this motion signal can be isolated from the Doppler radar module signal by comparing the received Doppler radar module signal and the received ultrasonic signal and removing the difference between the two signals, leaving only the desired thorax motion of respiration in the radar device channel. The ability to match exactly the two radar signals is due to the fact that microwaves propagate at $3.0 \times 10^8$ meters per second while sound waves propagate at approximately $3.5 \times 10^2$ meters per second.

Accordingly, in some embodiments, the ultrasonic radar module (112) operates on a frequency that produces the exact same Doppler shift in air when it is moved as the radar detection device (100) produces at 10.525 GHz when it is moved in the same manner. Correspondingly, other than amplitude, the baseband phase shift produced by both systems is the same. Further, the ultrasonic radar module (112) and the Doppler radar module (120) are configured to produce similar beamwidths. Therefore, when the ultrasonic radar module (112) is mounted to the radar detection device (100), both produce identical phase shifted signals except for the following case where a subject is positioned behind a non-conducting opaque barrier, such as a wall or door.

In that case, the primary reflection point for the ultrasonic radar module (112) is the outer surface of the wall, and the primary reflecting surface for the Doppler radar module (120) and antenna (125) is the wall surface. However, a portion of the Doppler radar module signal is also transmitted through the wall and reflected off of the subject, unlike the ultrasonic radar signal which is reflected off the wall only.

In some alternative embodiments of the invention, a pulsed ultrasonic radar signal is transmitted by the ultrasonic radar module (112) that is the reference module. The pulsed ultrasonic radar module (112) provides an accurate indication of the range or distance of the wall from the ultrasonic radar module (112) by measuring time of flight of the transmitted pulse of ultrasonic energy. In particular, motion of the handheld radar detection device (100) is measured by determining the small changes in range between each pulse versus time.

With this accurate range information provided as a function of time and with the knowledge of the frequencies that the Doppler radar module (120) is operating at, the stabilization processor (114) builds a model of an equivalent or synthetic Doppler signal using the information provided by the ultrasonic radar module (112). This synthetic Doppler signal, or phase shift, is fed to the motion compensation circuit (150) where it is used to cancel the radar clutter signal generated by the scanning motion of the radar detection device (100). Here, the radar signal output of the Doppler radar module (120) is delayed in time and the phase change output from the mathematical model is removed from the delayed signal. Note, in other embodiments, range data may be determined using other range finding techniques (e.g., laser technology) that provides accurate range resolution besides ultrasonic signals. Accordingly, a model of a synthetic Doppler signal may be generated from range data from other techniques in the same general manner stated above.

Overall, once motion has been cancelled, the motion compensated signal containing the respiration signal is next fed to a digital signal processor (180), where signal processing is performed to extract the respiration signal or "respiration signature." The radar detection device's signal processing circuit (180) detects the very small phase shift between the transmitted and received signal (caused by the motion of the thorax during the respiration cycle). The output of the digital signal processor (180) is amplified by an amplifier (160) to a level that can be used by a display processor (170). The display processor (170) formats the signal into a format that will drive a display unit (175).

Since much of the processing is preferably transparent to the user, this dictates that a simple but meaningful display system should be used. The display system preferably is visible in the dark and the level of illumination should be automatically controlled so the presence of user, such as a police officer, is not made known by a bright display illumination. The display unit (175) may be a liquid crystal or light emitting diode bar graph that shows an indication of probability of human presence as a function of the number of segments in the bar that are lit. The bar graph may also show modulation of a respiration event by displaying the amplitude of the signal being modulated at a respiration rate. It is also anticipated that the display may incorporate an alphanumeric capability to provide data to the user regarding detection probabilities, respiration rates, and other information that can be processed from the data.

Accordingly, in some embodiments, the radar detection device operates in the following manner: The user holds the device with a pistol-grip handle, pulls a trigger, and the device runs a 3-second self-test to verify that it is properly functioning. The user sees the results as a bar graph on a small LED display built into the device. While the trigger is held on by the operator, the radar detection device's 16-degree radar beam sends out a continuous wave or carrier of electromagnetic energy from the Doppler radar module (120) and the ultrasonic radar module (112) sends out an ultrasonic beam. Then, the return signals from each are detected and read by highspeed signal processing technology that quickly delivers bar-graph results to the user's display. As the person on the other side of the wall breathes, the bar-graph display rises and falls with a rhythmic response.

Figure 2:
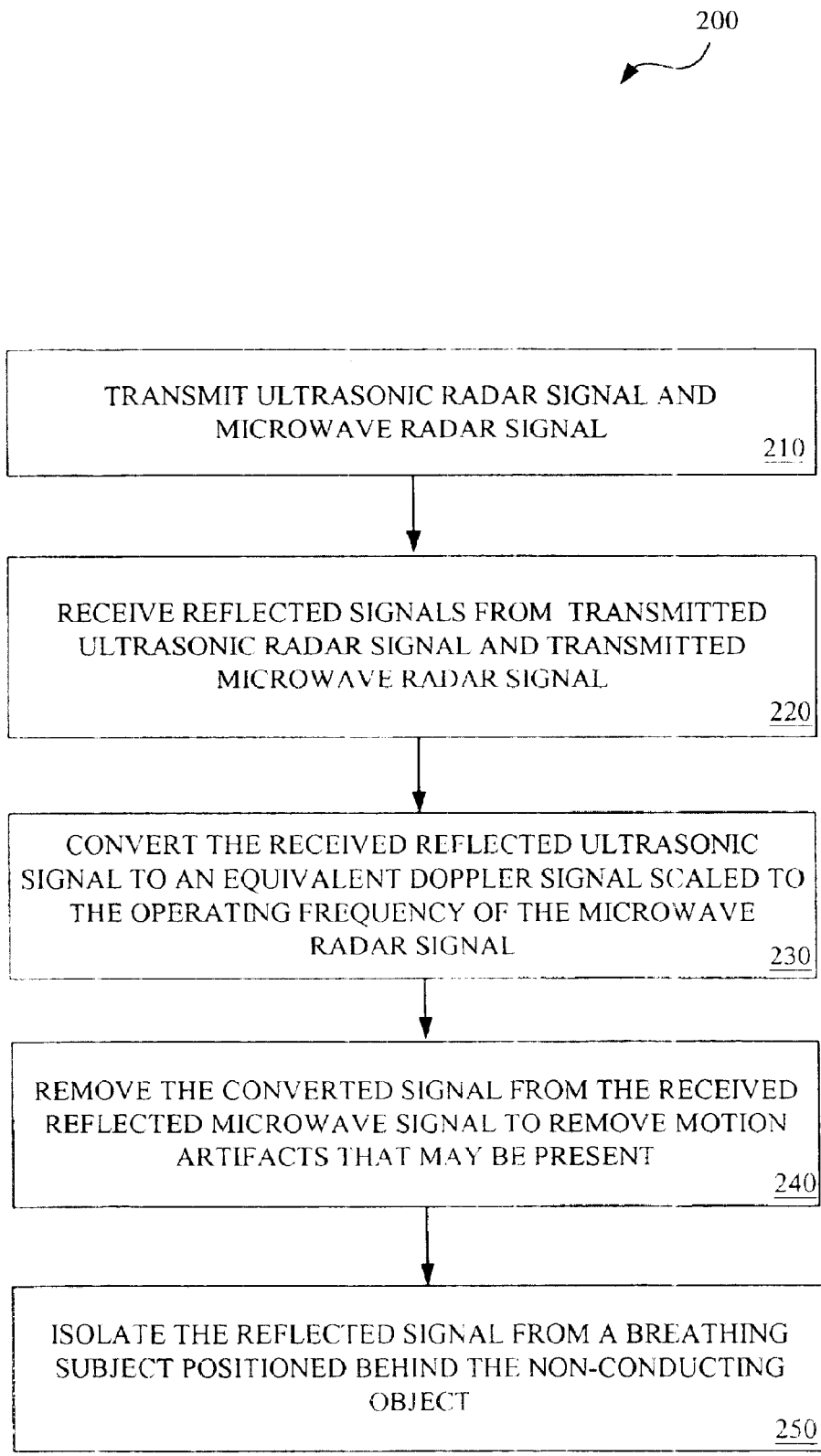
FIG. 2 is a flowchart depicting the functionality of the radar detection system employing the stabilization system of FIG. 1.

As depicted in FIG. 2, the functionality of a representative embodiment of the radar detection device (100) employing one embodiment of the stabilization system (110) or method (200) may be construed as beginning at block 210. In block 210, respective signals are transmitted from a reference module, such as an ultrasonic radar module (112), and a Doppler radar module (120) toward a non-conducting object. In block 220, the respective reflected signals from the non-conducting object (such as a wall) or some other obstructive object for each transmitted signal is received by the ultrasonic radar module (112) and Doppler radar module (120). Note, the received Doppler signal may include reflected energy from a living and breathing subject positioned behind the non-conducting object. In block 230, from the signal received by the ultrasonic radar module (112), a phase shift due to motion of the radar detection device (100) is determined. Next, in block 240, the phase shift due to motion of the radar detection device (100) is removed from the signal received by the Doppler radar module (120) to compensate for motion artifacts that may have been produced by movement of the Doppler radar module and an obstruction, such as a wall. Accordingly, in block 250, the reflected signal from a breathing subject positioned behind the non-conducting object is isolated.

Figure 3:
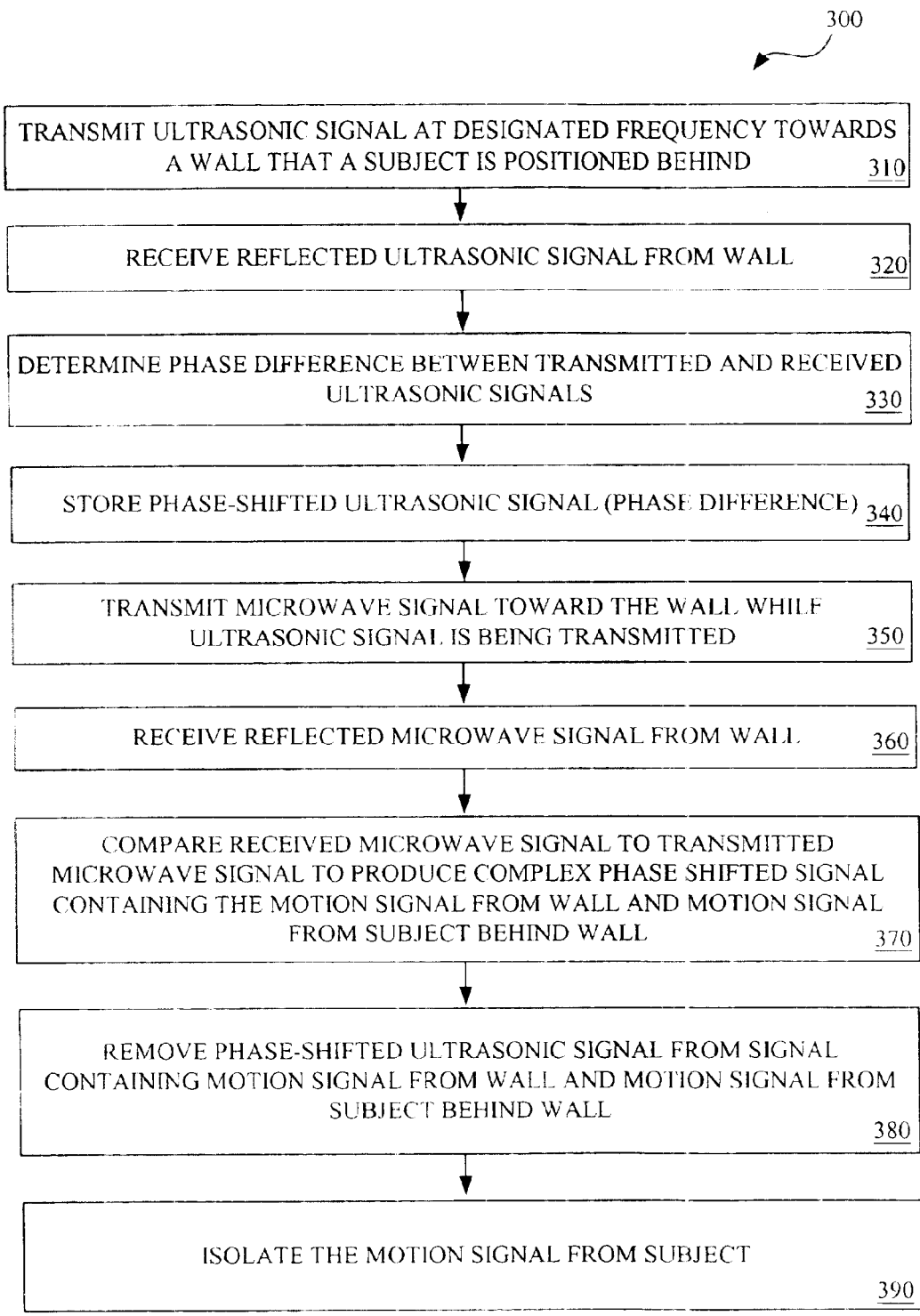
FIG. 3 is a flowchart depicting the functionality of the radar detection system employing the stabilization system of FIG. 1.

Referring now to FIG. 3, shown is a flowchart illustrating another embodiment (300), among others, of the operation of the present invention in detecting the presence of a living person behind an obstruction, such as a wall. In block 310, a continuous beam of sonic energy (of a frequency selected to match the propagation frequency of the microwave signal transmitted by the radar detection device (100)) is transmitted from the ultrasonic radar module (112) towards a wall behind which a subject is located. The ultrasonic energy does not penetrate the wall and is reflected from the wall back to the receiver of the ultrasonic radar module (112), as shown in block 320. Any hand motion of the radar detection device (100), on which the ultrasonic radar module (112) is mounted, produces a phase shift that varies directly as the hand motion changes toward and away from the wall. This phase-shifted ultrasonic signal is determined from the difference between the phase of the transmitted frequency and the phase of the received frequency of the ultrasonic signals, as shown in block 330. Correspondingly, in block 340, the phase-shifted ultrasonic signal is sent to and stored in a holding buffer, for example.

Next, in block 350, a microwave signal is transmitted (by the Doppler radar module (120)) toward the wall behind which a subject may be located while the ultrasonic signal is being transmitted. For the microwave signal, some of energy from the transmitted microwave signal reflects off of the wall and is received by the Doppler radar module (120), as shown in block 360. The reflected energy from the wall contains both an operator's hand motion and the motion of the breathing subject. In block 370, the received microwave signal is compared to the transmitted microwave signal, the product of which, produces a complex phase shifted signal containing both the motion signal from the wall reflection and from the subject's body behind the wall.

In block 380, the phase-shifted ultrasonic signal from the wall is removed from the mixed microwave radar signal containing both the signal from the wall due to hand motion and the signal from the subject behind the wall. After removal, the remaining microwave signal is the signal from the moving thorax of the subject. Thus, the respiration signature of the subject may be isolated, as shown in block 390.

Figure 4:
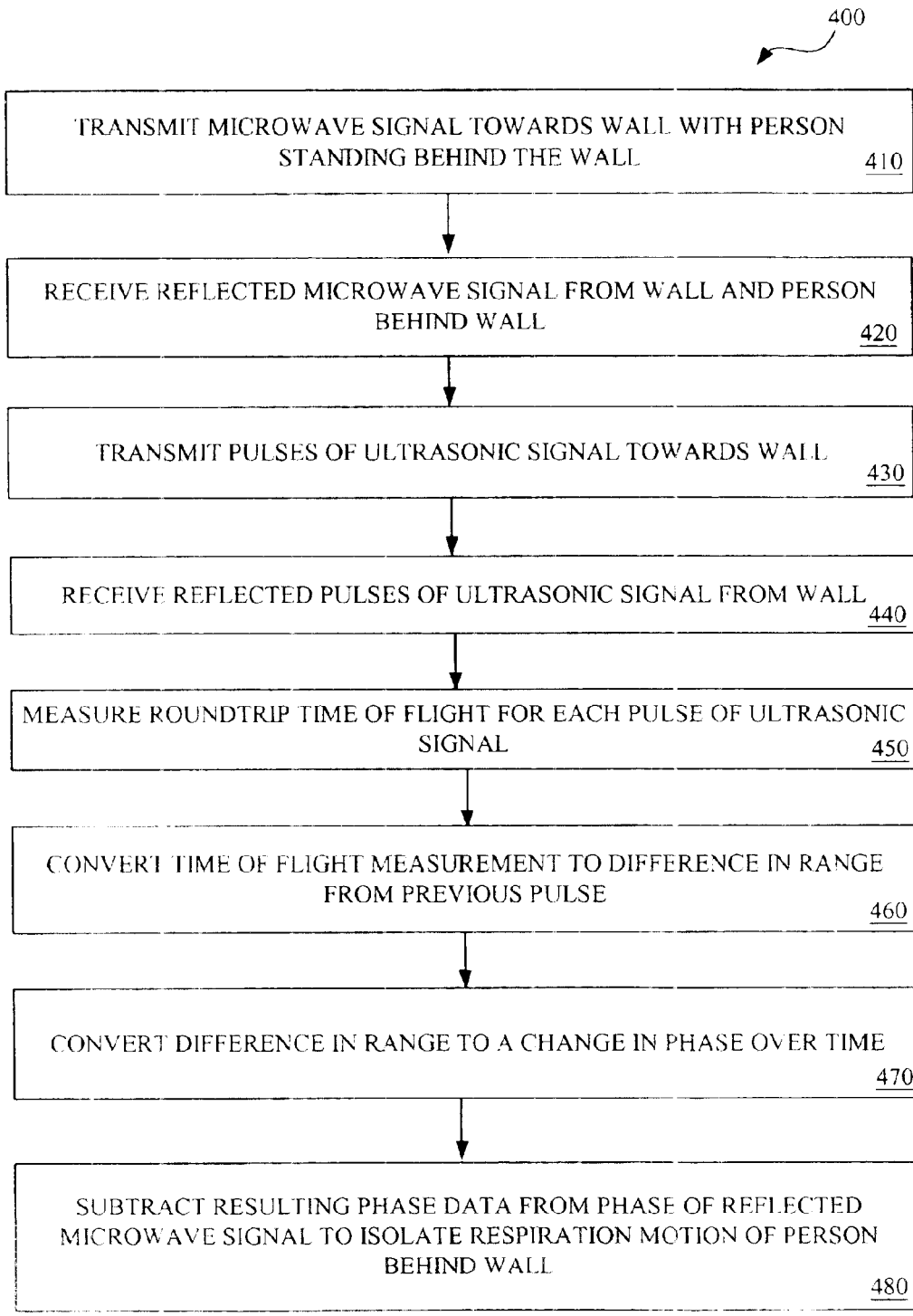
FIG. 4 is a flowchart depicting the functionality of the radar detection system employing the stabilization system of FIG. 1.

Referring now to FIG. 4, shown is a flowchart illustrating another embodiment (300), among others, of the operation of the present invention utilizing synthetic modeling. First, in block 410, a beam of continuous microwave energy is transmitted towards a target area such as a wall with a human subject standing behind the wall. Next, in block 420, the beam is received as a reflected microwave signal from the wall and the slightly moving subject behind the wall. Further, in block 430, a short pulse of ultrasonic energy is transmitted towards the target area and received as a reflected ultrasonic signal from the wall, as shown in block 440.

Roundtrip time of flight is measured for each pulse transmitted by the ultrasonic radar, as show in block 450.

Further, the time of flight of the successive reflected ultrasonic pulses is converted from time of flight to difference in range from the previous pulse, as shown in block 460, by determining the small changes in range to equivalent change in phase as a function of time. Next, in block 470, the difference in range is submitted to a mathematical model that converts change in range between the ultrasonic radar to the wall to an equivalent change in phase for the Doppler radar module (120) operating at a specific frequency. The resulting phase data that is output by the model is removed (e.g., by a subtraction operation) from the phase of the reflected microwave signal containing both hand motion from the wall and the respiration motion from the thorax of the subject behind the wall, as shown in block 480. Thus, the subtraction operation cancels the hand motion that is common to both radar signals.

Therefore, the synthetic model of the Doppler signal may be viewed as one channel of information based on the high-resolution range data from the ultrasonic radar module (112). Another channel of information, then, is the Doppler radar module (120) and its associated signals. By mixing the two channels and subtracting them, the remaining information is free of motion artifacts from movement of the radar detection device (100). Note, in other embodiments, high-resolution range data may be obtained using other range finding techniques, such as laser technology, among others.

Figure 5:
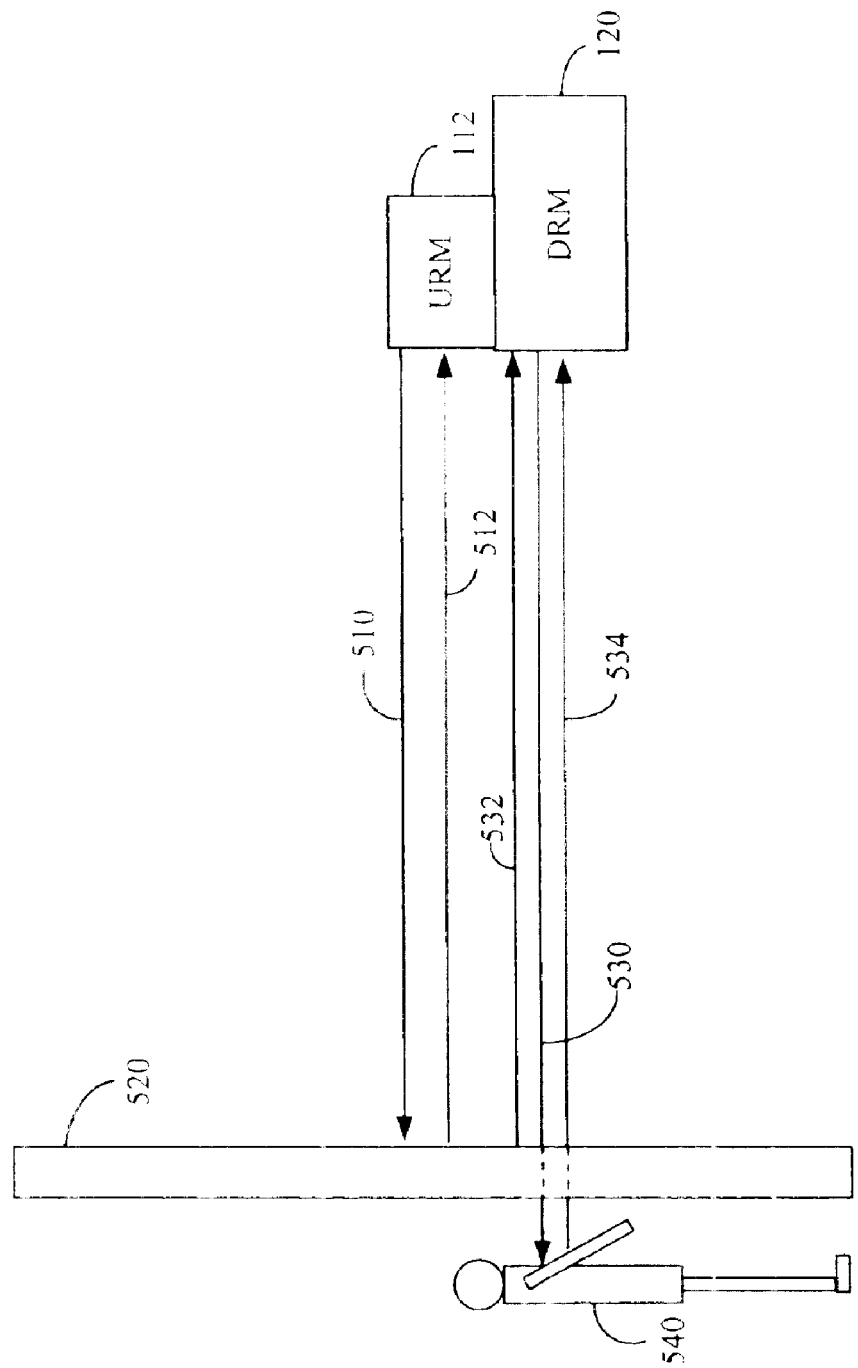
FIG. 5 is a block diagram depicting the operation of the radar detection system employing the stabilization system of FIG. 1 in detecting a person positioned behind an opaque reflective surface.

FIG. 5 shows an ultrasonic radar module (112) that is positioned on top of a Doppler radar module (120). Each module is in motion towards the opaque reflective surface (520) (e.g., a wall or door). The ultrasonic radar module (112) transmits a signal (510) towards the opaque reflective surface (520). Accordingly, the ultrasonic radar module (112) detects and receives a signal (512) reflected back from the reflective surface (520).

Next, consider that the Doppler radar module (120) transmits a microwave signal (530) toward the opaque reflective surface (520) and the person (540) positioned behind the opaque reflective surface (520). Correspondingly, a portion of the transmitted signal is reflected back off of the opaque surface (520) towards the Doppler radar module (120). This reflected signal (532) is detected and received by the Doppler radar module (120). The microwave power that is reflected from the opaque reflective surface (520) is amplified using a DC amplifier (130) and recorded at sample points by a data collection system (not shown).

Figure 6:
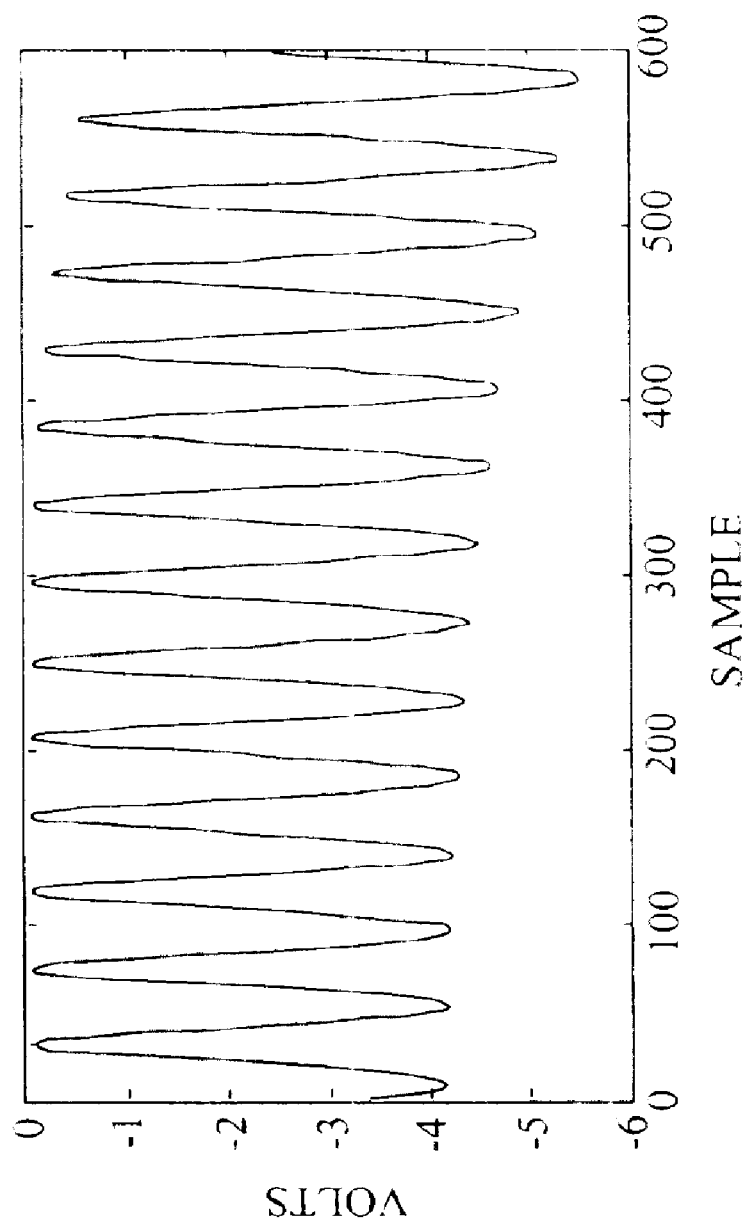
FIG. 6 is a plot of the pattern produced by power reflecting from the opaque reflective surface of FIG. 5 as a Doppler radar module is moved toward the opaque reflective surface.

Next, FIG. 6 shows a pattern produced by the power reflecting from the opaque reflective surface (520) as the Doppler radar module (120) is moved toward the opaque surface (520). The power received at the point at which the radar detection device's movement starts is at the left of FIG. 6. The power received from the opaque surface (520) when the radar detection device (100) reaches its closest approach to the opaque reflective surface (520) appears at the right side of the plot. For this particular example, the data represent the power returned from a brick wall.

One complete 360-degree sine wave is generated when the radar detection device (100) moves 1.75 centimeters (one half wavelength) toward the wall. Further, there are approximately 13.5 cycles of data confirming that the total movement of the radar detection device (100) was 23.7 centimeters or 9.3 inches. The shift in the sine pattern downward occurs due to a shift in the DC level as the radar detection device (100) approaches the wall. This shift is due to the fact that as more power is received from the approaching wall, the detector diode generates an increasing amount of rectified negative DC voltage, which biases the plot downward. The sine wave pattern is produced by an additive and subtractive change in phase between the direct path signal fed directly to the mixer of the radar detection device (100) and the reflected path from the antenna (125) to the wall and back to the antenna (125).

Referring again to FIG. 5, a portion of the transmitted signal is transmitted through the opaque reflective surface (520) towards the person (540) positioned behind the reflective surface (520). This portion of the transmitted signal is reflected off of the person's body (e.g., thorax), as the person is breathing, back towards the Doppler radar module (120). This reflected signal (534) is then received by antenna (125) and detected by Doppler radar module (120). The power received from the reflective surface (520) by the Doppler radar module (120) is amplified and converted to a voltage that is sampled by a data collection system. The range data from the ultrasonic radar module (112) is also simultaneously sampled at the same point.

In some embodiments, the range generated by the ultrasonic radar module (112) may be available from both a numeric counter that provides range to two decimal places and also on a transistor to transistor logic (TTL) line. The TTL line is pulsewidth modulated. The width of the range pulse corresponds to the range of the transducer of the ultrasonic radar module to a target, which is the reflective surface (520) in FIG. 5. High resolution range data may be developed from the pulsewidth modulated data by starting a high speed counter when the line goes high and stopping the counter when the line returns to the low logic state. The pulsewidth modulator may provide range data with an accuracy on the order of millimeters. Interestingly for the case where the reflective surface is a door, the resolution of the range data may be high enough to allow the relief of decorative panels on the door to be observed in the range data as the ultrasonic transducer is moved across the slight change in door surface elevation.

Figure 7:
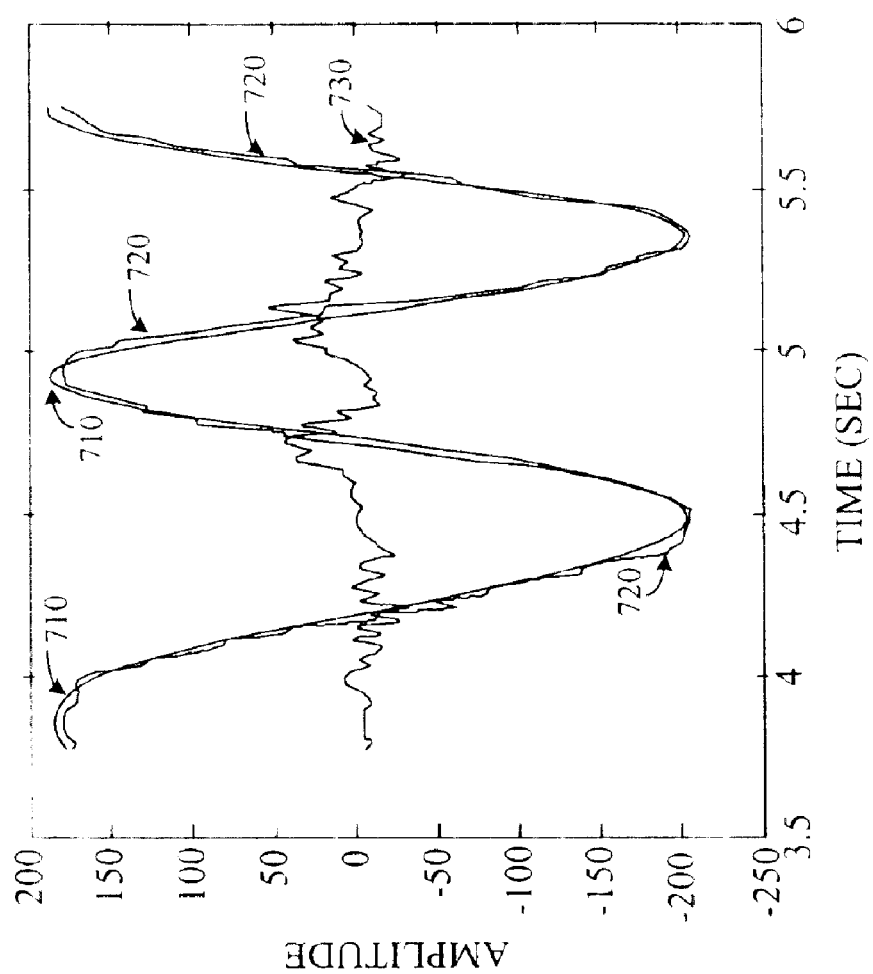
FIG. 7 is a plot of the pattern produced by removing motion artifacts that were recorded in FIG. 5 as the Doppler radar module was moved toward the opaque reflective surface.

The high resolution ultrasonic range data may be converted to a synthetic phase modulated signal scaled to the radar detection device's operating frequency of 10.525 GHz, using a simple Doppler model called the "Range to Phase Model." The conversion of the range data using the model produces a synthetic phase signal similar to the one shown in FIG. 6. Once computed, the synthetic phase data generated from the range information may be removed from the measured output signal from the Doppler radar module (120) using signal processing (e.g., a subtraction operation). FIG. 7 shows the result of this operation.

Referring to FIG. 7, the trace indicated by pointer 710 corresponds to the amplified output of the radar detection device's mixer that was recorded as the radar detection device (100) moved toward the wall. The Range to Phase Model ("synthetic phase data"), indicated by pointer 720, is removed from the radar detection device signal (710) and the difference is shown and is indicated by pointer 730.

This plot shows that the amplitude difference ("motion cancellation factor") between the motion artifact signal level produced between trace 730 and trace 710 is approximately 3. A cancellation factor of 3 is generally sufficient to detect human movement behind the wall on a selected basis and is indicative of a respiration signature (730) of the subject (540) behind the wall (520). Higher cancellation performance may also be increased by reducing the beam size of the ultrasonic radar module (112) to provide a beamwidth that is closer to the beamwidth of the Doppler radar module (120), if possible.

Since the stabilization system (110) employed on the radar detection device (100) compensates for motion artifacts generated by self-induced motion from the radar detection device (100), it presents a preferred way to operate the radar detection device (100) in a handheld mode that requires no wall or tripod for stabilization. When operated in this mode, the radar detection device (100) may be hand held and located some distance from the intervening door or wall. It may be slowly scanned across the wall or door that the subject of interest would be concealed behind and detect the respiration patterns of the subject from a remote distance.

Additionally, the radar detection device can detect the body movement of a subject at longer ranges than those at which the respiration signature can be detected when the subject is stationary. Note, total body motion presents a much larger Doppler modulated radar cross section than the small respiration induced movement of the chest wall. However, for law enforcement applications, for example, the subject cannot be depended upon to voluntarily move during the search process. Thus, the detection of the involuntary respiration signature is advantageous in ensuring that a motionless subject can be detected.

The signal processing components and modules of embodiments of the present invention can be implemented in hardware, software, firmware, or a combination thereof. If implemented in hardware, as in preferred embodiments, the signal processing components can be implemented with any or a combination of the following technologies, which are all well known in the art: a discrete logic circuit(s) having logic gates for implementing logic functions upon data signals, an application specific integrated circuit (ASIC) having appropriate combinational logic gates, a programmable gate array (s) (PGA), a field programmable gate array (FPGA), etc. In alternative embodiments, the signal processing components are implemented in software or firmware that is stored in a memory and that is executed by a suitable instruction execution system.

Any process descriptions or blocks in flow charts should be understood as representing modules, segments, or portions of code which include one or more executable instructions for implementing specific logical functions or steps in the process, and alternate implementations are included within the scope of the preferred embodiment of the present invention in which functions may be executed out of order from that shown or discussed, including substantially concurrently or in reverse order, depending on the functionality involved, as would be understood by those reasonably skilled in the art of the present invention.

It should be emphasized that the above-described embodiments of the present invention, particularly, any "preferred" embodiments, are merely possible examples of implementations, merely set forth for a clear understanding of the principles of the invention. Many variations and modifications may be made to the above-described embodiment(s) of the invention without departing substantially from the spirit and principles of the invention. All such modifications and variations are intended to be included herein within the scope of this disclosure and the present invention and by the following claims.

Therefore, having thus described the invention, at least the following is claimed:

1. A system for suppressing motion artifacts introduced by movement of a radar detection device, comprising:
   a microwave radar module for directing a beam of microwave energy towards an object and for receiving reflected microwave energy comprising a reflected microwave signal from the object;
   a reference module for directing a reference beam of energy towards the object and for receiving reference energy comprising a reflected reference signal from the object; and
   a signal processor to suppress the motion artifacts in the reflected microwave energy after analyzing the reflected microwave energy and the reflected reference energy.

2. The system of claim 1, wherein the beamwidth of the beam of microwave energy transmitted by the microwave radar module is substantially the same as the beamwidth of the reference beam of energy transmitted by the reference module.

3. The system of claim 1, wherein the microwave radar module operates at a frequency higher than 10 GHz.

4. The system of claim 1, wherein the object is a non-conducting object, the beam of microwave energy transmits through the non-conducting object, and the reference beam of energy does not transmit through the non-conducting object.

5. The system of claim 1, wherein:
   the reflected microwave energy further comprises a reflected microwave signal from a living subject positioned behind the object; and
   the signal processor detects a respiration signature of the living subject after the motion artifacts introduced by the movement of the radar detection device are suppressed.

6. The system of claim 5, further comprising:
   a display unit for indicating that the presence of the living subject positioned behind the object has been detected, wherein the signal processor determines that the living subject has been detected by analyzing the reflected microwave energy after the motion artifacts in the reflected microwave energy have been suppressed.

7. The system of claim 1, wherein:
   the microwave radar module directs a continuous beam of microwave energy;
   the reference module directs a continuous reference beam of energy; and
   the signal processor suppresses the motion artifacts by removing the difference between the reflected microwave energy and the reflected reference energy.

8. The system of claim 7, wherein the reference module directs a continuous reference beam of ultrasonic energy.

9. The system of claim 8, wherein the reference module operates at a frequency that produces substantially the same Doppler shift in air as the microwave radar module produces at an operating frequency of the microwave radar module.

10. The system of claim 1, wherein:
    the microwave radar module directs a continuous beam of microwave energy,
    the reference module directs a pulsed reference beam of energy; and
    the signal processor suppresses the motion artifacts by determining a representation of the reflected microwave signal from the object based on an operating frequency of the microwave radar module and distance information to the object provided by the reference module, the signal processor utilizing the representation to remove the motion artifacts from the reflected microwave energy.

11. The system of claim 10, wherein the representation of the reflected microwave signal is scaled to the operating frequency of the microwave radar module.

12. The system of claim 10, wherein the reference module directs a pulsed reference beam of ultrasonic energy.

13. The system of claim 10, wherein the reference module directs a pulsed reference beam of laser energy.

14. A system for suppressing motion artifacts introduced by movement of a radar detection device, comprising:

a first transmitting means for directing a first beam of microwave energy towards an object;

a second transmitting means for directing a reference beam of energy towards the object;

a first receiving means for receiving reflected microwave energy from the first beam of microwave energy, the reflected microwave energy from the first beam comprising a reflected microwave signal from the object;

a second receiving means for receiving reflected reference energy from the reference beam of energy, the reflected reference energy from the reference beam comprising a reflected reference signal from the object; and a signal processing means for suppressing the motion artifacts introduced by the movement of the radar detection device by analyzing the reflected microwave energy and the reflected reference energy.

15. The system of claim 14, wherein:

the reflected microwave further comprises a reflected microwave signal from a living subject positioned behind the object; and the signal processing means detects a respiration signature of the living subject after the motion artifacts are removed from the reflected microwave energy of the first beam.

16. The system of claim 15, further comprising:

a means for indicating that the presence of the living subject positioned behind the object has been detected, wherein the signal processor determines that the subject has been detected by analyzing the reflected microwave energy after the motion artifacts in the reflected microwave energy have been suppressed.

17. The system of claim 14, wherein the object is a non-conducting object, the first beam of microwave energy transmits through the non-conducting object, and the reference beam of energy does not transmit through the non-conducting object.

18. The system of claim 14, wherein the beamwidth of the first beam of microwave energy is substantially the same as the beamwidth of the reference beam of energy.

19. The system of claim 14, wherein the first transmitting means for directing operates at a frequency higher than 10 GHz.

20. The system of claim 14, wherein:

the first transmitting means directs a continuous beam of microwave energy;

the second transmitting means module directs a continuous reference beam of energy; and the signal processor means suppresses the motion artifacts by removing the difference between the reflected microwave energy and the reflected reference energy.

21. The system of claim 20, wherein the second transmitting means directs a continuous reference beam of ultrasonic energy.

22. The system of claim 21, wherein the second transmitting means operates at a frequency that produces substantially the same Doppler shift in air as the first transmitting means produces at an operating frequency of the first transmitting means.

23. The system of claim 14, wherein:

the first transmitting means directs a continuous beam of microwave energy;

the second transmitting means directs a pulsed reference beam of energy; and the signal processing means suppresses the motion artifacts by determining a representation of the reflected microwave signal from the object based on an operating frequency of the first transmitting means and distance information to the object provided by the second receiving means, the signal processing means utilizing the representation to remove the motion artifacts from the reflected microwave energy.

24. The system of claim 23, wherein the representation of the reflected microwave signal is scaled to the operating frequency of the first transmitting means.

25. The system of claim 23, wherein the second transmitting means directs a pulsed reference beam of ultrasonic energy.

26. The system of claim 23, wherein the second transmitting means directs a pulsed reference beam of laser energy.

27. A method for suppressing motion artifacts introduced by movement of a radar detection device, comprising the steps of:

transmitting a first beam of microwave energy towards an object;

receiving reflected energy from the first beam of microwave energy, the reflected microwave energy from the first beam comprising a reflected microwave signal from the object;

transmitting a reference beam of energy towards the object;

receiving reflected reference energy from the reference beam of energy, the reflected reference energy from the reference beam comprising a reflected reference signal from the object; and suppressing the motion artifacts introduced by movement of the radar detection device in the reflected microwave energy.

28. The method of claim 27, wherein the beamwidth of the first beam of microwave energy is substantially the same as the beamwidth of the reference beam of energy.

29. The method of claim 27, wherein the first beam is transmitted at a frequency higher than 10 GHz.

30. The method of claim 27, further comprising the step of:

detecting a respiration signature of a living subject positioned behind the object after the motion artifacts are suppressed, wherein the reflected microwave energy from the first beam further comprises a reflected microwave signal from the living subject.

31. The method of claim 30, further comprising the step of:

indicating that the presence of the living subject positioned behind the object has been detected by analyzing the reflected microwave energy of the first beam after the motion artifacts in the reflected microwave energy of the first beam have been suppressed.

32. The method of claim 27, wherein the object is non-conducting object, the first beam of microwave energy transmits through the non-conducting object, and the reference beam of energy does not transmit through the non-conducting object.

33. The method of claim 27, the suppressing step further comprising the step of:

removing the difference between the reflected microwave energy and the reflected reference energy, wherein the first beam of microwave energy is a continuous beam of microwave energy, and the reference beam of energy is a continuous reference beam of energy.

34. The method of claim 33, wherein the continuous reference beam of energy is a continuous reference beam of ultrasonic energy.

35. The method of claim 34, wherein the continuous reference beam of energy is transmitted at a frequency that produces substantially the same Doppler shift in air as the continuous beam of microwave energy does.

36. The method of claim 27, the suppressing step further comprising the steps of:

obtaining range information on the distance to the object from the reflected reference energy;

generating a representation of the reflected microwave signal from the object using the range information; and comparing the representation of the reflected microwave signal from the object with the reflected microwave energy from the first beam to isolate a reflected microwave signal from a different object, wherein the first beam of microwave energy is a continuous beam of microwave energy and the reference beam of energy is a pulsed reference beam of energy.

37. The method of claim 36, wherein the representation of the reflected microwave signal is scaled to the same frequency as the first beam of microwave energy.

38. The method of claim 36, wherein the pulsed reference beam of energy is a pulsed reference beam of ultrasonic energy.

39. The method of claim 36, wherein the pulsed reference beam of energy is a pulsed reference beam of laser energy.

* * * * *